United States Patent [19]

Wolcott

[11] Patent Number: 4,981,567

[45] Date of Patent: Jan. 1, 1991

[54] LITHIUM-SALT REFERENCE HALF-CELL FOR POTENTIOMETRIC DETERMINATIONS

[75] Inventor: Duane K. Wolcott, Baton Rouge, La.

[73] Assignee: The Dow Chemical Company, Midland, Mich.

[21] Appl. No.: 328,817

[22] Filed: Mar. 24, 1989

Related U.S. Application Data

[63] Continuation of Ser. No. 32,213, Mar. 30, 1987, abandoned, which is a continuation-in-part of Ser. No. 876,328, Jun. 19, 1986, abandoned.

[51] Int. Cl.$^5$ ............................................. G01N 27/26
[52] U.S. Cl. ............................ 204/153.1; 204/153.21; 204/433
[58] Field of Search ............... 204/1 R, 416, 1 T, 420, 204/433, 435

[56] References Cited

U.S. PATENT DOCUMENTS

| | | | |
|---|---|---|---|
| 3,103,480 | 9/1963 | Watanabe et al. | 204/416 |
| 4,166,021 | 8/1979 | Ross, Jr. et al. | 204/435 |
| 4,333,810 | 6/1982 | Wllcott | 204/431 |
| 4,401,548 | 8/1983 | Brezinski | 204/435 |

OTHER PUBLICATIONS

Ives et al., *Reference Electrodes*, (1961), pp. 155, 156, 181, 203, 449–451.
Grove—Rasmussen, K. V., *Acta Chem. Scand.* 5 (1951), 422–430.

*Primary Examiner*—John F. Niebling
*Assistant Examiner*—Ben C. Hsing
*Attorney, Agent, or Firm*—Reginald F. Roberts, Jr.

[57] ABSTRACT

The present invention provides an electrolyte solution, a reference half-cell, and a complete electrochemical cell particularly useful in making pH measurements of industrial and waste streams having suspended solids or high salt concentrations. An electrolyte solution containing water; at least one lithium salt, e.g. lithium chloride; and at least one ionic species at a constant electrochemical potential, e.g. silver chloride, buffered to a constant pH, is used in the half-cell and complete electrochemical cell. A high concentration of total ions in the electrolyte solution provides a flow direction out of the cell into the test stream, thereby reducing or eliminating the problems of cell contamination and plugging previously encountered. A second solution of high total ionic concentration, e.g. lithium nitrate, is also provided as a salt bridge in the cells to further insure diffusion of the cell electrolyte solution out into the stream being tested.

2 Claims, 2 Drawing Sheets

LITHIUM-SALT REFERENCE HALF-CELL FOR POTENTIOMETRIC DETERMINATIONS

CROSS-REFERENCE TO RELATED APPLICATION

This is a continuation of application Ser. No. 32,213 filed Mar 30, 1987, which is a continuation-in-part of application Ser. No. 876,328 filed June 19, 1986, both now abandoned.

BACKGROUND OF THE INVENTION

The present invention relates to potentiometric analytical determinations. More particularly, the invention relates to a method and to an instrument for determining the pH of liquid streams.

The measurement of pH is commonly effected with a commercial pH meter using a glass electrode. This instrument measures the potential difference developed between the glass electrode and a reference electrode of constant electrical potential. The potential difference when the electrodes are removed from a standard solution and placed in a test solution is related to a difference in pH.

Immersion-type electrodes are the most commonly used electrodes. These are roughly cylindrical, and comprise a barrel or stem of inert glass which is sealed at the lower end to a tip, often hemispherical, of special pH-responsive glass. This type of electrode is used in conjunction with a separate reference electrode to complete the electrochemical cell.

Combination electrodes, which are a consolidation of the pH-responsive glass electrode and reference electrode in a single probe, are now commonly being provided in a coaxial arrangement with the reference-electrode compartment surrounding the pH sensor. Theoretical considerations favor combination electrodes which have a cylindrical symmetry and a steady state of diffusion.

The electrical circuit of a probe or pH cell is completed through a salt bridge that usually consists of a concentrated solution of potassium chloride. The solution makes contact at one end with the test solution, and at the other end with the reference electrode. A liquid junction is formed at the area of contact between the salt bridge and the test solution.

The pH-responsive surface of the glass electrode consists of a thin membrane formed from a special glass which, after suitable conditioning, develops a surface potential that is an accurate index of the hydrogen-ion concentration of the solution in which the electrode is immersed. To permit changes in the potential of the active surface of the glass membrane to be measured, an inner reference cell of constant potential is disposed on the opposite side of the glass membrane The inner reference cell comprises a solution that has a stable concentration of hydrogen ions, e.g. a buffered solution of potassium chloride which contains counter-ions to which the inner electrode is reversible. The inner electrode commonly consists of a silver - silver chloride or a calomel electrode in a buffered solution of potassium chloride.

For the reference half-cell, a silver electrode comprising silver and silver chloride provides a highly reproducible potential in the potassium chloride bridge solution, and is the most frequently used reference electrode for process measurement, although calomel and thallium half-cells have also been used.

The above prior-art devices serve very well for measuring the pH of dilute aqueous solutions which are substantially free of suspended solids. In many industrial streams, however, this condition is not satisfied. In particular, it has been found that such devices are subject to frequent fouling, contamination, and plugging when used to monitor the pH of streams containing suspended particulate matter, high concentrations of salts such as calcium chloride, or both.

SUMMARY OF THE INVENTION

In general, the present invention in one aspect provides a chemical composition useful as an electrolyte solution in a reference half-cell for making potentiometric measurements. The composition comprises a solution in water of at least one lithium salt and at least one ionic species of constant electrochemical potential.

In a second aspect, the invention provides a reference half-cell for the potentiometric determination of an ionic species in an external liquid environment. The half-cell comprises a hollow casing impervious to the external liquid environment. The casing is sealed at one end with a cap and at the other end with a porous material of low diffusivity. An electrolyte solution is disposed within the casing. The solution is characterized as a solution in water of at least one lithium salt and at least one ionic species of constant electrochemical potential. A reversible electrode is disposed within the hollow casing and is in contact with the electrolyte solution. The electrode is responsive to the ionic species of constant electrochemical potential. The reversible electrode is connected to an electrical lead which passes through a passageway in the cap. The other end of the electrical lead is suitably connected to an electrical meter o other measuring device.

In another aspect, the invention provides a second embodiment of a reference half-cell for the potentiometric determination of an ionic species in an external liquid environment. The second embodiment comprises a hollow casing impervious to the external liquid environment. The casing is sealed at one end with a cap and at the other end with a porous material of low diffusivity. A porous partition of low diffusivity divides the casing into first and second compartments. The first compartment extends from the partition to the end of the casing sealed with the cap. A first electrolyte solution is disposed within the first compartment. The solution is characterized as a solution in water of at least one lithium salt and at least one ionic species of constant electrochemical potential. A second electrolyte solution is disposed in the second compartment. The second solution is characterized as water saturated with lithium nitrate at a temperature of from about 0° C. to about 40° C. A reversible electrode is disposed within the first compartment, and is in contact with the first electrolyte solution. The electrode is responsive to the ionic species of constant electrochemical potential. An electrical lead is threaded through a passageway in the cap, and is connected to the reversible electrode. The other end of the lead is connected to an electrical device such as an electrometer.

In still another aspect, the present invention provides an electrochemical cell for the potentiometric determination of an ionic species in an external liquid environment. The electrochemical cell comprises a first hollow casing impervious to the external liquid environment.

The casing is sealed at one end with a cap, and at the other end with a porous material of low diffusivity. A second hollow casing is spaced apart from, and disposed within, the first hollow casing, thereby defining a cavity between said first and second casings. If the second hollow casing is coaxially disposed within the first hollow casing, the cavity is an annular space of generally uniform cross-sectional area. If the second hollow casing is eccentrically disposed within the first hollow casing, the cavity has a nonuniform cross-section. For ease of fabrication the second hollow casing is preferably coaxial with the first hollow casing. The cavity is sealed at one end with a porous material of low diffusivity. The second hollow casing is sealed at one end with an ion-selective material. The other end of the second casing and the other end of the annular cavity are sealed with a cap. A first reversible electrode is disposed within the second hollow casing. A second reversible electrode is disposed within the annular cavity. An electrolyte solution is disposed within the second hollow casing and the cavity, and is in contact with the reversible electrodes. The solution is characterized as a solution in water of at least one lithium salt, a first ionic species of constant electrochemical potential, and a second ionic species to which the ion-selective material is reversible. A first electrical lead passes through a first passageway in the cap, and is connected to the first reversible electrode. A second electrical lead passes through a second passageway in the cap, and is connected to the second reversible electrode. Both leads are also connected to an electrical device such as an electrometer.

In still another aspect, the present invention provides a second embodiment of an electrochemical cell for the potentiometric determination of an ionic species in an external liquid environment. The second embodiment of the cell comprises a first hollow casing impervious to the external liquid environment. The casing is sealed at one end with a cap, and at the other end with a porous material of low diffusivity. A second hollow casing is spaced apart from, and disposed within, the first hollow casing, thereby defining a cavity between the first and second casings. If the second hollow casing is coaxially disposed within the first hollow casing, the cavity is an annular space of generally uniform cross-sectional area. If the second hollow casing is eccentrically disposed within the first hollow casing, the cavity has a nonuniform cross-section. For ease of fabrication the second hollow casing is preferably coaxial with the first hollow casing. The cavity is sealed at one end with a porous material of low diffusivity. The second hollow casing is sealed at one end with an ion-selective material. The other end of the second hollow casing and the other end of the cavity are sealed with the cap. A porous partition of low diffusivity divides the annular cavity between the first and second hollow casings into first and second compartments. The first compartment extends from the cap to the partition, and the second compartment from the partition to the end of the cavity which is sealed with the porous material. A first reversible electrode is disposed within the second hollow casing, and a second reversible electrode within the first compartment of the cavity. A first electrolyte solution is disposed in the second hollow casing and in the first compartment of the cavity, and is in contact with the electrodes. The first solution is characterized as a solution in water of at least one lithium salt, a first ionic species having a constant electrochemical potential with respect to the first reversible electrode, and a second ionic species to which the ion-selective material is reversible. A second electrolyte solution is disposed in the second compartment of the cavity. The second solution is characterized as water saturated with lithium nitrate at a temperature of from about 0° C. to about 40° C. A first electrical lead passes through a first passageway in the cap, and is connected to first reversible electrode. A second electrical lead passes through a second passageway in the cap, and is connected to the second reversible electrode. The other ends of the electrical leads are connected to an electrical measuring device.

In addition to providing a versatile electrochemical half-cell and complete potentiometric cell, the present invention provides a solution to the specific problems found in the background art: namely, contamination of the reference half-cell, and plugging of the half-cell and the salt bridge. These and other aspects of the invention will be apparent to those skilled the art from the foregoing description and from the more detailed description which follows.

DESCRIPTION OF THE PREFERRED EMBODIMENTS

Figure 1:
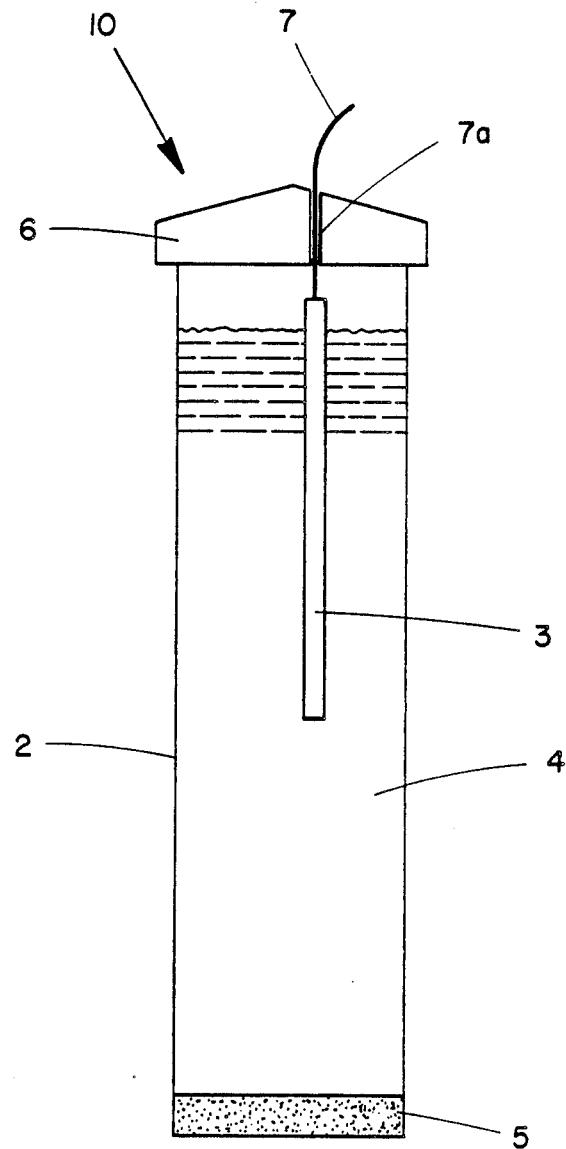
FIG. 1 is a schematic representation illustrating a reference half-cell made in accordance with the principles of the present invention.

The following description illustrates the manner in which the principles of the present invention are applied, but is not to be construed as in any sense limiting the scope of the invention.

When a pH probe is used to measure the pH of industrial streams containing high salt concentrations, the flow of electrolyte is predominantly from the solution of higher concentration to that of lower concentration. Accordingly, since many such streams have salt concentrations substantially greater than that attainable with potassium chloride at ambient temperatures, the flow is predominantly from the industrial stream into the cell. Besides the contamination of the cell electrolyte which results therefrom, this inwardly-directed flow often causes plugging of the cell, particularly when the industrial stream includes relatively high concentrations of suspended solids. Because lithium salts are appreciably more soluble than potassium salts, the present invention provides a cell which contains solutions with salt concentrations which are higher than those of most industrial streams, thereby providing a flow direction out of the cell and eliminating the problems inherent in the prior-art cells.

As illustrated in the following detailed description, an improvement is provided in a reference half-cell to be used, in combination with an ion-selective half-cell and a salt bridge, for determining the concentration of an ion to which the ion-selective half-cell is responsive. The reference half-cell includes a reversible electrode in contact with an aqueous electrolyte solution. The improvement includes (a) an aqueous solution of a lithium halide saturated with lithium nitrate at about 0°–40° C. and at least one ionic species of constant electrochemical potential, as the solution in contact with the reversible electrode; and (b) a salt bridge comprising a solution of water saturated with lithium nitrate at about 0°–40° C. The concentration of lithium halide in the solution contacting the reversible electrode is from about three to about four moles per liter of solution from about three to about four molar). Preferably, the concentration of lithium halide is at least about 3.5 molar. The salt bridge solution preferably has a total ionic concentration substantially equal to or higher than the total ionic concentration of the reference half-cell electrolyte solution, to insure diffusion of the electrolyte solutions in the cell out into the solution being tested. While the salt in the bridge solution is preferably lithium nitrate, other lithium salts are possibly useable: but the nitrate offers fewer problems such as precipitation by contaminants in the process stream.

The preferred embodiments of the present invention comprise:

(a) A chemical composition useful as an electrolyte solution in a reference half-cell for potentiometric measurements. The solution is characterized as a solution of a lithium halide, and optionally lithium nitrate. The concentration of the lithium halide is preferably at least about 3.5 molar, although lower concentrations may be used less effectively. The solution is saturated with lithium nitrate at a temperature of from about 0° C. to about 40° C., with the lower temperature being preferred.

(b) A reference half-cell for the potentiometric determination of an ionic species in an external liquid environment. The half-cell includes a reversible electrode, and an electrolyte solution in contact with the reversible electrode. The solution is characterized as a solution in water of a lithium halide and optionally lithium nitrate. Additionally, the solution contains at least one ionic species of constant electrochemical potential. The concentration of the lithium halide is preferably at least about 3.5 molar. The solution is saturated with lithium nitrate at a temperature of from about 0° C. to about 40° C., with the lower temperature being preferred. In a first embodiment, the reversible electrode is a silver / silver halide, mercury / mercurous halide, or thallium / thallous halide electrode: and the halide of the lithium halide is the same halide as the silver, mercurous, or thallous halide. The preferred halide is chloride. In a second embodiment, the lithium halide is lithium iodide: and the reversible electrode is an iodine/iodide/platinum electrode. While other inert metals may be used, platinum is preferred.

(c) A reference half-cell for the potentiometric determination of an ionic species in an external liquid environment. The half-cell includes a reversible electrode, and first and second electrolyte solutions. The first solution contacts the reversible electrode. The first solution is characterized as a solution in water of a lithium halide and optionally lithium nitrate. Additionally, the solution contains at least one ionic species of constant electrochemical potential. The concentration of the lithium halide is preferably at least about 3.5 molar. While lower concentrations may be used, they are less effective. The solution is saturated with lithium nitrate at a temperature of from about 0° C. to about 40° C., with the lower temperature being preferred. In a first embodiment, the reversible electrode is a silver / silver halide, mercury / mercurous halide, or thallium / thallous halide electrode: and the halide of the lithium halide is the same halide as the silver, mercurous, or thallous halide. The preferred halide is chloride. In a second embodiment, the lithium halide is lithium iodide: and the reversible electrode is an iodine/iodide/platinum electrode. While other inert metals may be used, platinum is preferred. The second electrolyte solution is water saturated with lithium nitrate at a temperature of about 0° C. to about 40° C., with the lower temperature preferred.

(d) An electrochemical cell for the potentiometric determination of an ionic species in an external liquid environment. The electrochemical cell includes first and second reversible electrodes in contact with an electrolyte solution. The solution is characterized as a solution in water of a lithium halide and optionally lithium nitrate. Additionally, the solution contains at least one ionic species of constant electrochemical potential. The concentration of the lithium halide is preferably at least about 3.5 molar, although lower concentrations may be used. The solution is saturated with lithium nitrate at a temperature of from about 0° C. to about 40° C., with the lower temperature being preferred. In a first embodiment, the first and second reversible electrodes are silver / silver halide, mercury / mercurous halide, or thallium / thallous halide electrodes: and the halide of the lithium halide is the same halide as the silver, mercurous, or thallous halide. The preferred halide is chloride. In a second embodiment, the lithium halide is lithium iodide: and the first and second reversible electrodes are iodine/iodide/platinum electrodes.

(e) An electrochemical cell for the potentiometric determination of an ionic species in an external liquid environment. The electrochemical cell includes first and second reversible electrodes in contact with a first electrolyte solution. A second electrolyte solution acts as a salt bridge for the electrochemical cell. The first solution is characterized as a solution in water of a lithium halide and optionally lithium nitrate. Additionally, the solution contains at least one ionic species of constant electrochemical potential. The concentration of the lithium halide is preferably at least about 3.5 molar, although lower concentrations may be used. The solution is saturated with lithium nitrate at a temperature of from about 0° C. to about 40° C., with the lower temperature preferred. In a first embodiment, the first and second reversible electrodes are silver / silver halide, mercury / mercurous halide, or thallium / thallous halide electrode: and the halide of the lithium halide is the same halide as the silver, mercurous, or thallous halide. The preferred halide is chloride. In a second embodiment, the lithium halide is a lithium iodide; and the first and second reversible electrodes are iodine/iodide/platinum electrodes. The second electrolyte solution is water saturated with lithium nitrate at a temperature of from about 0° C. to about 40° C., with the lower temperature being preferred.

More specifically, reference is made to FIG. 1 which shows a half-cell 10 useful in making potentiometric measurements. The half-cell 10 is provided with a hollow casing 2 which is impervious to aqueous solutions. The casing 2 is sealed at one end with a porous material 5 of low diffusivity, and is closed at its other end by a cap 6 which includes a passageway 7a for an electrical lead 7. Casing 2 defines a compartment 4 in which is disposed an aqueous electrolyte solution buffered to a constant pH. This solution contains at least one lithium halide (e.g. about 3.5 moles per liter) and at least one ionic species of constant electrochemical potential. A reversible electrode 3 is in contact with the solution, and is connected to the electrical lead 7, which is also connected to an electrical meter (not shown). An ion-selective half-cell may be used in conjunction with a separate reference half-cell similar to half-cell 10 where a coaxial probe configuration is not desired or cannot be used.

Figure 2:
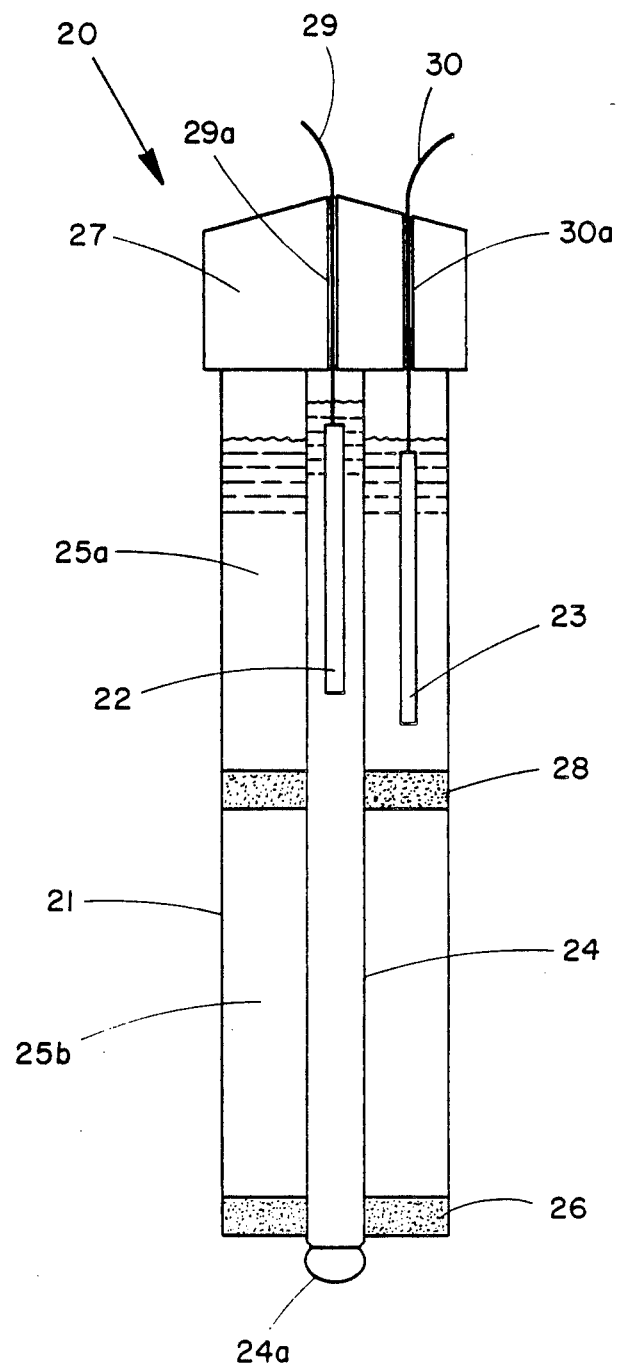
FIG. 2 is a schematic representation illustrating an electrochemical cell made in accordance with the principles of the invention.

Reference is now made to FIG. 2, which illustrates an electrochemical cell 20 made in accordance with the principles of the present invention. The cell 20 comprises a hollow outer casing 21 which is impervious to aqueous solutions. Disposed coaxially in the casing 21 is a second hollow casing 24; e.g., a glass tube. For this specific application, the casing or tube 24 may beneficially be made, at least in part, of alkali-resistant glass. The casing 24 terminates in a bulb 24a which is sensitive to the ion to be potentiometrically measured.

The coaxial casing 21 and tube 24 define therebetween an annular cavity which is separated by a porous partition 28 of low diffusivity into first and second compartments 25a and 25b, respectively. The end of the tube 24 which terminates in the bulb 24a extends beyond one end of the casing 21, to facilitate contact with the test solution. That end of the casing 21, is sealed with a plug 26 made of a porous material of low diffusivity. Preferably, the material used to form the partition 28 and plug 26 is porous poly(tetrafluoroethylene). Materials such as this, including many others such as glass frits and wood fibers, are well known in the art and need not be described here in detail. The diffusion characteristics of such materials are also well known in the art.

A first solution comprising a solution in water of at least one lithium salt and at least one ionic species of constant electrochemical potential, is disposed in the hollow interior of the tube 24 and in the first compartment 25a. A second solution, comprising water saturated with lithium nitrate at about 0°–40° C., is disposed in the second compartment 25b. A first electrical lead 29 passes through a first passageway 29a in cap 27. The first lead 29 is connected to a reversible electrode 22 which is in contact with the first solution in electrode 24. A second reversible electrode 23, which serves as a reference electrode, is disposed in the first compartment 25a, in contact with the first solution. A second electrical lead 30 passes through a second passageway 30a in the cap 27, and is connected to the reversible electrode 23. The first and second electrodes 22 and 23 are preferably silver electrodes. The first and second leads 29 and 30 are also connected to an electrical meter (not shown).

If the ion to be determined is the hydrogen ion, the first solution is buffered to a constant pH. This solution is preferably made by the following procedure or its equivalent: (a) preparing a solution of lithium chloride in water, the concentration of lithium chloride characterized as from about three moles per liter to about four moles per liter, and preferably as at least about 3.5 moles per liter of solution: and (b) saturating the solution of lithium chloride with lithium nitrate and adding silver nitrate (which forms a solution saturated with silver chloride and lithium nitrate), preferably at a temperature of about 0° C. to ensure stability at ambient temperatures. The solution is buffered during either of the above steps by the addition of lithium salts of suitable buffering capability. For example, a suitable buffering system for providing a pH of 10 comprises the combination of lithium carbonate and lithium bicarbonate at molar concentrations of about 0.025. Many other buffering systems are well-known and widely used in the analytical arts, and are suitably employed in this invention to obtain various pH's. The second solution is preferably saturated at a temperature of about 0° C. with lithium nitrate to ensure stability at ambient temperatures. It is also beneficial to add about one percent by weight of a gelling agent such as a carboxyethylcellulose ether or fumed silica to the first and second solutions, in order to increase the viscosity of the solutions and slow down the diffusion thereof.

A particularly important application of the cell 20 is the determination of the pH of industrial streams containing high concentrations of salts, and contaminated by suspended solids. For this application it has been found that a potentiometric instrument using a probe similar to Cell 20 gives about four times the length of trouble-free service as prior-art cells which utilize potassium chloride as an electrolyte solution.

The total ionic concentrations of the first and second solutions are preferably maintained substantially equal, but the concentration of the second solution may be higher than the concentration of the first solution. The concentration of the lithium halide in the first solution is preferably at least about 3.5 molar. In addition, the first solution preferably has a composition characterized as saturated with lithium nitrate and silver chloride at about 0° C., and the second solution has a composition characterized as saturated at about 0° C. with lithium nitrate.

While certain representative embodiments and details have been shown for the purpose of illustrating the present invention, it will be apparent to those skilled in the art that various changes and modification can be made therein without departing from the spirit and scope of the invention.

What is claimed is:

1. A potentiometric method to determine the concentration of an ion in a concentrated aqueous salt solution without contaminating an aqueous solution of an electrolyte disposed in a potentiometric reference half-cell or plugging the reference half-cell, comprising the steps of:
   (a) disposing in the reference half-cell a concentrated aqueous solution of a lithium halide containing at least about three and one-half moles of the lithium halide per liter of solution and, at a constant electrochemical potential, the ion whose concentration is to be determined;
   (b) disposing the reference half-cell in the concentrated aqueous salt solution containing the ion whose concentration is to be determined, thereby providing a higher salt concentration within the reference half-cell than in the external salt solution, thus preventing a significant flow of the external salt solution into the reference half-cell; and
   (c) measuring the electrical potential between (1) a first electrode in contact with the electrolyte solution in the reference half-cell, the first electrode being responsive to the concentration of the ion to be determined; and (2) a second electrode in contact with the external salt solution, the second electrode also being responsive to the concentration of the ion to be determined, thereby determining the concentration of the ion without contaminating the concentrated aqueous solution of the lithium halide and without plugging the reference half-cell.

2. The method of claim 1, wherein the concentrated aqeuous solution of the lithium halide in the half-cell is saturated with lithium nitrate at a temperature of about 0° to about 40° C.

* * * * *